United States Patent [19]

Taylor et al.

[11] 4,182,710

[45] Jan. 8, 1980

[54] KETENIMINE INTERMEDIATES FOR 6α-METHOXY-α-CARBOXY PENICILLINS

[75] Inventors: Andrew W. Taylor, Reigate; George Burton, Sutton; John P. Clayton, Horsham, all of England

[73] Assignee: Beecham Group Limited, England

[21] Appl. No.: 808,825

[22] Filed: Jun. 22, 1977

[30] Foreign Application Priority Data

Jun. 26, 1976 [GB] United Kingdom ............... 26720/76

[51] Int. Cl.$^2$ .......................................... C07D 277/04
[52] U.S. Cl. ................................ 260/245.2; 424/246; 424/271; 260/239.1
[58] Field of Search ................ 260/306.7 C, 239.1 TB

[56] References Cited

U.S. PATENT DOCUMENTS

| | | | |
|---|---|---|---|
| 3,860,585 | 1/1975 | Carroll et al. | 260/306.7 C |
| 3,960,845 | 1/1976 | Hiraoka et al. | 260/239.1 TB |

FOREIGN PATENT DOCUMENTS 1463468 2/1977 United Kingdom .

*Primary Examiner*—Nicholas S. Rizzo
*Attorney, Agent, or Firm*—Jacobs & Jacobs

[57] ABSTRACT

A class of ketenimine intermediates are prepared from 6-acylaminopenicillins having an α-carboxy substituent in the side-chain, and are useful in the preparation of 6α-methoxy-α-carboxy penicillins.

15 Claims, No Drawings

KETENIMINE INTERMEDIATES FOR 6α-METHOXY-α-CARBOXY PENICILLINS

This invention relates to a class of intermediates useful for the preparation of antibacterially active penicillin derivatives, in particular 6α-methoxy penicillin having a carboxylic acid function at the 2-position in the side-chain. The invention also relates to a process for the preparation of the novel intermediates and to a process for their conversion to the penicillin.

British Patent Specification No. 1,463,468 discloses a process for the preparation of 6-alkoxy penicillins which comprises reacting a 2-hydroxy- or 2-halopenicillin with a halogenating agent to form a 2,3-dihaloimine and subsequently reacting this with an alkali metal alkoxide to give a 6-alkoxyketenimine which is hydrated to give the required product. One disadvantage of this process is that the 2-hydroxy- or 2-halopenicillin starting material must be prepared by acylation of 6-amino penicillanic acid with the corresponding side-chain. The process does not provide a method for the introduction of a 6α-alkoxy substituent directly into a 6-acylaminopenicillin.

Furthermore in the above process the 2,3-dihaloimine intermediate must be isolated in order to remove excess halogenating agent (such as phosphorus pentachloride) therefrom prior to treatment with the alkali metal alkoxide. However in the case of a penicllin derivative having a carboxylic acid function at the 2-position, the dihaloimine is thermally unstable and the process is therefore unsuitable for that class of penicillins.

The present invention is concerned with a process which enables 2-carboxy acetamido penicillin derivatives to be converted into their 6α-methoxy analogues. The key intermediates for this process are novel ketenimines.

Accordingly the present invention provides a ketenimine of formula (I):

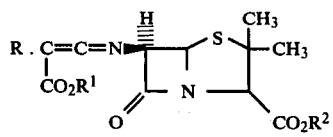

wherein

R represents a furyl, thienyl, cycloalkyl, cycloalkenyl or phenyl group, or a phenyl group substituted with from 1 to 3 hydroxy, halogen, nitro, $C_1$–$C_6$ alkyl, $C_1$–$C_6$ alkoxy, amino or carboxy groups;

$R^1$ represents an ester-forming radical; and $R^2$ represents an in vivo hydrolysable ester forming radical or a carboxyl-blocking group.

Suitable groups R include 2- and 3- furyl, 2- and 3-thienyl, cyclopropyl, cyclobutyl, cyclopentyl, cyclohexy, cyclobutenyl, cyclopentenyl, cyclohexenyl, cyclohexa-1, 4-dienyl, phenyl, 4-hydroxyphenyl, 3-chloro-4-hydroxphenyl, 3,4-hydroxyphenyl.

Most suitably R is 2- or 3-thienyl, phenyl or 4-hydroxyphenyl; preferably phenyl.

In vivo hydrolysable pharmaceutically acceptable ester forming radicals for the group $R^2$ are those which, when attached at that position on a penicillin nucleus, hydrolyse readily in the human body to produce the parent acid. It is well established that simple alkyl and aryl esters of penicillins fail to meet this requirement as they are resistant to hydroylsis by human tissues. Examples of suitable in vivo hydrolysable ester radicals for the group $R^2$ include acyloxyalkyl groups such as acetoxymethyl, pivaloyloxymethyl, α-acetoxyethyl, α-acetoxybenzyl and α-pivaloyloxyethyl groups; alkoxycarbonyloxyalkyl groups, such as ethoxycarbonyloxymethyl and α-ethoxycarbonyloxyethyl; and lactone, thiolactone and dithiolactone groups, i.e. ester groups of formula:

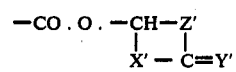

wherein X' and Y' are oxygen or sulphur and Z' is an ethylene group or a 1,2-phenylene group optionally substituted by lower-alkoxy, halogen or nitro.

Preferred ester groups are the phthalide and 5,6-dimethoxyphthalide esters.

Suitable carboxyl-blocking derivatives for the group $R^2$ in formula (I), include salts, ester, and anhydride derivatives of the carboxylic acid. The derivative should be one which may readily be cleaved at a later stage of the reaction. Suitable salts include tertiary amine salts, such as those with tri-loweralkylamines. N-ethyl-piperidine, 2,6-lutidine, pyridine, N-methylpyrrolidine, dimethylpiperazine. A preferred salt is with triethylamine.

Suitable carboxyl-blocked groups of formula $CO_2R^2$ include the following:

(i) —$COOCR_cR_dR_e$ wherein at least one of $R_c$, $R_d$ and $R_e$ is an electron-donor e.g. p-methoxyphenyl, 2,4,6-trimethylphenyl, 9-anthryl, methoxy, acetoxy, methoxymethyl, benzyl or fur-2-yl. The remaining $R_c$, $R_d$ and $R_e$ groups may be hydrogen or organic substituting groups. Suitable ester groups of this type include p-methoxybenzyloxy-carbonyl, 2,4,6-trimethylbenzyloxy carbonyl, bis-(p-methoxyphenyl)methoxycarbonyl, 3,5-di-t-butyl-4-hydroxybenzyloxycarbonyl, methoxymethoxycarbonyl and benzyloxycarbonyl.

(ii) —$COOCR_cR_dR_e$ wherein at least one of $R_c$, $R_d$ and $R_e$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R_c$, $R_d$ and $R_e$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) —$COOCR_cR_dR_e$ wherein at least two of $R_c$, $R_d$ and $R_e$ are hydrocarbons such as alkyl e.g. methyl or ethyl, aryl, e.g. phenyl and the remaining $R_c$, $R_d$ and $R_e$ group, if there is one, is hydrogen. Suitable esters of this type include t-butyloxycarbonyl, t-amyloxycarbonyl, diphenylmethoxycarbonyl and triphenylmethoxycarbonyl.

(iv) —$COOCR_f$ wherein $R_f$ is adamantyl, 2-benzyloxyphenyl, 4-methylthiophenyl, tetrahydrofur-2-yl-tetrahydropyran-2-yl, pentachlorophenyl;

(v) Silyloxycarbonyl groups obtained by reaction of a silylating agent as described above with the carboxylic acid group;

(vi) $CO_cP.R_aR_b$, wherein $R_a$ is an alkyl, haloalkyl, aryl, aralkyl, alkoxy, haloalkoxy, aryloxy, aralkyloxy or dialkylamino group, $R_b$ is the same as $R_a$ or is halogen or $R_a$ and $R_b$ together form a ring.

The carboxyl group may be regenerated from any of the above esters by usual methods for example, acid - and base - catalysed hydrolysis, or by enzymically - catalysed hydrolysis. Alternative methods of cleavage include:

reaction with Lewis acids, such as trifluoroacetic acid, formic acid, hydrochloric acid in acetic acid, zinc bromide in benzene and aqueous solutions or suspensions or mercuric compounds. (The reaction with the Lewis acid may be facilitated by addition of a nucleophile such as anisole);

reduction with agents such as zinc/acetic acid, zinc/formic acid, zinc/lower alcohol, zinc/pyridine, palladised-charcoal and hydrogen, and sodium and liquid ammonia;

attack by nucleophiles, such as those containing a nucleophilic oxygen or sulphur atom for example alcohols, mercaptans and water; oxidative methods, for example those which involve the use of hydrogen peroxide and acetic acid; and irradiation.

The group $R^1$ may be any ester-forming radical as hydrolysis to the free acid at that position is not essential for the activity of the eventually produced penicillin derivative. The group $R^1$ may therefore be any of the radicals described above as being in vivo hydrolysable when present at the 3-position of the penicillin nucleus; or it be any of the above-mentioned carboxyl-blocking groups.

In addition the group $R^1$ may be an alkyl, cycloalkyl, alkenyl, alkynyl, aryl, or heterocyclic group any of which may be substituted. Suitable such groups include:

(a) alkyl especially $C_{1-6}$ alkyl such as methyl, ethyl, n- and iso-propyl, n-, sec-, iso- and tert-butyl, and pentyl;

(b) substituted $C_{1-6}$ alkyl wherein the substituent is at least one of: chloro, bromo, fluoro, nitro, carbo ($C_{1-6}$ alkoxy), $C_{1-6}$ alkanoyl, $C_{1-6}$ alkoxy, cyano, $C_{1-6}$ alkylmercapto, $C_{1-6}$ alkylsulfinyl, $C_{1-6}$ alkylsulphonyl, 1-indanyl, 2-indanyl, furyl, pyridyl, 4-imidazolyl, phthalimido, azetidino, aziridino, pyrrolidino, piperidino, morpholino, thiomorpholino, N-($C_{1-6}$ alkyl)-piperazino, pyrrolo, imidazole, 2-imidazolino, 2,5-dimethylpyrrolidino, 1,4,5,6-tetrahydropyrimidino, 4-methylpiperidino, 2,6-dimethylpiperidino, alkylamino, dialkylamino, alkanoylamino, N-alkylanilino, or substituted N-alkylanilino wherein the substituent is chloro, bromo, $C_{1-6}$ alkyl or $C_{1-6}$ alkoxy;

cycloalkyl and ($C_{1-6}$ alkyl) substituted cycloalkyl having from 3 to 7 carbon atoms in the cycloalkyl moiety;

(d) alkenyl having up to 8 carbon atoms;

(e) alkynyl having up to 8 carbon atoms;

(f) phenyl and substituted phenyl wherein the substituent is at least one of chloro, bromo, fluoro, $C_{1-6}$ alkoxy, $C_{1-6}$ alkanoyl, carbo-($C_{1-6}$)alkoxy, nitro, or di($C_{1-6}$)alkyl amino;

(g) benzyl or substituted benzyl wherein the substituent is chloro, bromo, fluoro, $C_{1-6}$ alkyl, $C_{1-6}$ alkoxy, $C_{1-6}$alkanoyl carbo($C_{1-6}$)alkoxy, nitro, or di($C_{1-6}$)alkylamino;

(h) heterocyclic groups such as: furyl, quinolyl, methyl-substituted quinolyl, phenazinyl, 1,3-benzodioxolyl, 3-(2-methyl-γ-pyronyl), 3-(γ-pyronyl) or methylpyridyl;

(i) other hydrocarbyl groups such as: ac - indanyl and substituted derivatives thereof wherein the substituent is methyl, chloro or bromo; ac -tetrahydronaphthyl and substituted derivatives thereof wherein the substituent is methyl, chloro or bromo; benzohydryl, trityl, cholesteryl, or bicyclo[4.4.0]decyl.

Preferred groups for $R^1$ include $C_{1-6}$ alkyl, benzyl, phthalidyl, indanyl, phenyl, mono-, di-, and tri-($C_1-C_6$)- alkyl substituted phenyl such as o-, m or p-methylphenyl, ethylphenyl, n- or iso- propylphenyl, n-, sec-, iso- or t- butylphenyl.

The intermediates of formula (I) may be prepared by reacting a 6-acylaminopenicillin of formula (II):

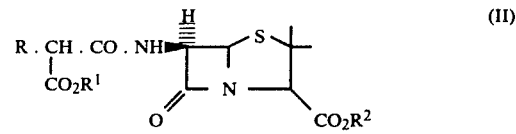

wherein R, $R^1$, and $R^2$ are as defined with respect to formula (I) above; with an acid halide.

Suitably the reaction with acid halide is carried out in the presence of an acid binding agent such as a tertary amine, e.g. pyridine, triethylamine or N-N-dimethylaniline.

Examples of suitable acid halides are phosphorus pentachloride, phosgene, phosphorous pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from +5° C. to −30° C. (preferably about 0° C.) when phosphorus pentachloride is employed. The amount of the tertiary amine is preferably 3–5 mols per mol of phosphorus pentachloride. It is also preferable to use the phosphorus halide in an amount in excess of that of the starting material. The value of the ketenimine compounds of formula (i) derives from their use in the preparation of 6-methoxy penicillins.

Thus in a further aspect, the present invention provides a process for preparing a compound of formula (III):

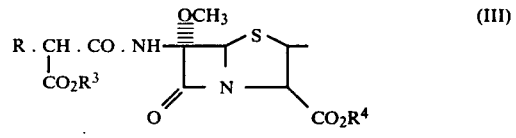

wherein R is as defined above with respect to formula (I) above;

$R^3$ represents hydrogen, a pharmaceutically acceptably salt forming ion or a pharmaceutically acceptable ester-forming radical; and $R^4$ represents hydrogen, a pharmaceutically acceptable salt-forming ion or in vivo hydrolysable ester-forming radical; which process comprises:

(a) reacting a ketenimine of formula (I) with a double-bond addition reagent;

(b) reacting the resulting product with a compound of formula $CH_3OM$, wherein M is an alkali metal or thallium;

(c) hydrolysing the resulting product;

(d) removing any carboxyl-blocking groups; and (e) optionally salifying or esterifying any free carboxylic acid group.

Suitable salt-forming ions for the groups $R^3$ and $R^4$ include metal ions e.g. aluminium, alkali metal ions such as sodium or potassium, alkaline earth metal ions such as calcium or magnesium, and ammonium or substituted ammonium ions for example those from lower alkylamines, such as triethylamine, hydroxy-lower alkylamines such as 2-hydroxyethylamine, bis-(2-hydroxyethyl)-amine or tri-(2-hydroxyethyl)-amine, cycloalkylamines such as dicyclohexylamine, or from procaine, dibenzylamine, N,N-dibenzylethylenediamine, 1-ephenamine, N-ethylpiperidine, N-benzyl-β-phenethylamine, dehydroabietylamine, N,N'-bis-dehydroabietylethylenediamine, or bases of the pyridine type such as pyridine, collidine or quinoline, or other amines which have been used to form salts with benzylpenicillin.

The double bond addition reagent is a difunctional moiety where each of the groups can be displaced by nucleophiles.

Suitable double bond addition reagents for the above process include diatomic halogen molecules or a compound of formula $Br.N_3$. If the double-bond addition reaction is designated X-Y, the adduct formed has the formula (IV):

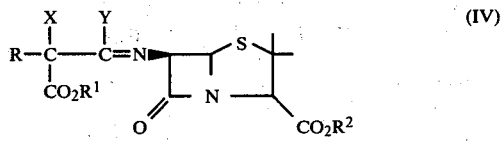

Suitably both X and Y are halogen, preferably chlorine, as the reaction proceeds more smoothly.

The reaction is suitably carried out in an inert solvent, such as tetrahydrofuran or a halogenated hydrocarbon e.g. chloroform, at low temperatures such as +20° C. to −100° C. preferably −50° C. to −80° C., e.g. at about −70° C.

The compound of formula (IV) is then reacted with an alkali metal or thallium methoxide of formula $CH_3OM$. Suitably M may be sodium or potassium, but is preferably lithium. The reaction is generally carried out in a polar aprotic solvent, preferably methanol, preferably in the presence of another inert solvent, such as tetrahydrofuran as long as it as it does not freeze at the temperature of the reaction. The reaction is suitably carried out at low temperature, preferably in the range −40° C. to 80° C., preferably about −75° C. The reagent $CH_3OM$ may be formed in situ by the use of methanol together with a base such as butyl lithium, lithium diisopropylamide, lithium or sodium hydride or preferably butyl lithium. Preferably the steps (a) and (b) above are carried out without the isolation of the compound (IV).

The thus produced 6-methoxy ketenimine of formula (V):

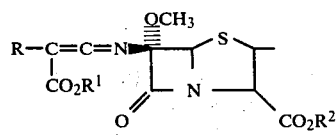

is then hydrolysed.

Preferably this hydrolysis is carried out at a pH in the range 1 to 5 preferably pH2 to 4, at ambient temperature. Suitable solvents include tetrahydrofuran or acetone.

The ketenimine compounds of formula (I) are also useful intermediates for the preparation of other 6-substituted penicillins.

Thus a compound of formula (VI):

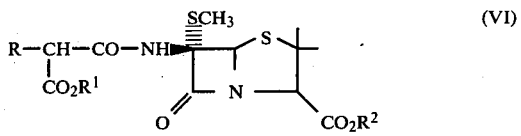

[wherein R, $R^1$, and $R^2$ are as defined with respect to formula (I)] may be prepared by:

(a) reacting a ketenimine of formula (I) with a compound of formula MeS-Z, wherein Z is a readily displaceable group; to produce a compound of formula (VII):

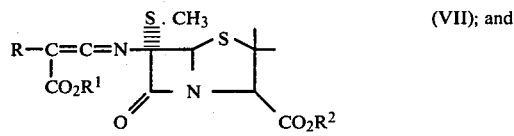

(b) hydrolysing the compound of formula (VII) to produce a 6-methylthio penicillin, of formula (VI).

A suitable readily displaceable group Z is the group $-SO_2CH_3$, and the reaction of compound (I) with compound MeS—Z is generally carried out at low temperature, suitably in the range of +5° C. to −30° C., preferably about 0° C.

The thiomethyl penicillins of formula (VI) are themselves useful intermediates for the preparation of other 6-substituted penicillins, including the methoxy-substituted compounds (III), by methods known in the art, for example by treatment with mercuric chloride and methanol.

The following examples illustrate the preparation of a ketenimine intermediate of this invention and its use in preparing antibacterially active penicillins.

"Carfecillin" is the penicillin of formula:

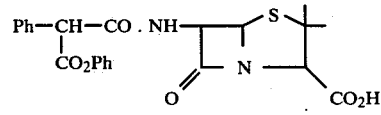

EXAMPLE 1

Preparation of p-nitrobenzyl 6β-(2'-phenyl-2'-phenoxycarbonyl)ketenimino penicillanate.

p-Nitrobenzyl 6β-(2'-phenyl-2'-phenoxycarbonyl)acetamido penicillanate (1.50 g., 2.54 mmol) in benzene (6 ml) was treated with pyridine (1.68 ml), added at 0° C. Phosphorus pentachloride (1.32 g., 6.36 mmol) in benzene (30 ml) was slowly added, with stirring at 0° C. After three hours at 0° C., the solution was filtered. The solids were washed with ether, and the combined organic layers washed successively with water and sodium bicarbonate solution, dried ($Na_2SO_4$) and evaporated to give almost pure title compound (1.23., 85%), μmax ($CHCl_3$) 2030, 1790, 1740, 1600, 1530, 1350 cm$^{-1}$. δ ($CDCl_3$), 1.36, 1.42, (6H, 2s, $(CH_3)_2C$), 4.56 (1H,s,$C_3$-proton), 5.43 (2H,s,—$CH_2$—), 5.77 (2H,s,$C_5$ and $C_6$-protons), 7.1–7.9 (12H, complex, aryl protons), 8.37 (2H,d,J. 8Hz., —CH—$CNO_2$—).

Hydrolysis of the title Ketenimine (aqueous T.H.F.: phosphoric acid) at pH 4 over 24 hours, followed by addition of ethyl acetate, which was washed with water, dried (Na$_2$SO$_4$) and evaporated, afforded starting p-nitrobenzyl 6β-(2'-phenyl-2'-phenoxycarbonyl)acetamido penicillanate only with no trace of the 6α-epimer.

EXAMPLE 2

Preparation of p-nitrobenzyl 6α-methoxy-6β-(2'-phenyl-2'-phenoxycarbonyl) Ketenimino penicillanate Method (i)

(a) p-Nitrobenzyl-6β-(1',2', dichloro-2'-phenyl-2'-phenoxycarbonyl)ethylideneamino penicillanate.

The Ketenimine from Example 1 (0.17g., 0.3mmol) in chloroform (3ml) at −50° C. was treated dropwise over 30 minutes with chlorine in chloroform until disappearance of max (CHCl$_3$) 2030cm$^{-1}$, concomitant with appearance of max (CHCl$_3$) 1670cm$^{-1}$. After evaporation, the title product was obtained.

(b) P-Nitrobenzyl 6α-methoxy-6β-(2'-phenyl-2'-phenoxycarbonyl)Ketenimino penicillanate.

The imino chloride from (a) above was immediately used in (b) because of its instability at room temperature. Thus the imino chloride was dissolved in tetrahydrofuran (T.H.F.) (2ml) and this solution added to lithium methoxide (51ml) in methanol (1ml): T.H.F. (12ml) at −75° C. After stirring for twenty minutes, acetic acid (0.5ml) was added, and the mixture warmed to room temperature. Ether was added and washed with sodium bicarbonate solution and water, dried and evaporated to give a residue which was chromatographed on silica (petrol/ethyl acetate), thus affording the desired title compound (0.045g, 25% for (a) and (b) overall), max (CHCl$_3$) 2030, 1790, 1730, 1600, 1530, 1500, 1350cm$^{-1}$. δ (CDCl$_3$) 1.28 (6H,s,(CH$_3$)$_2$C), 3.58 (3H,s,CH$_3$O—), 4.33 (1H,s,C$_3$-proton), 5.25 (2H,s,—CH$_2$Ar), 5.50 (1H,s,C$_5$-proton), 7.1–7.6 (12H,complex, aryl protons), 8.15 (2H,d,J 8Hz., —CH—CNO$_2$—).

Method (ii) (This method avoids isolation of unstable intermediates.)

The Ketenimine from Example 1 (0.25g., 0.44mmol) in T.H.F. (15Ml) at −75° C. was treated, with stirring, with bromine (0.024ml. 0.44mmol). After 10 minutes, lithium methoxide (99.88% purity) 65mg.) in methanol (1ml) was added, dropwise. After 10 minutes stirring at −75° C. acetic acid (0.5ml) was added, and the reaction solution worked up as in method (i) (b), thus affording the title compound (0.08g. 30%.

EXAMPLE 3

Preparation of 2'-epimers of p-nitrobenzyl 6α-methoxy-6β-(2'-phenyl)-2'-phenoxycarbonyl)acetamido penicillinanate.

Method (i)

The Ketenimine from Example 2 (0.05g) in T.H.F.: H$_2$O (20:1) (1ml) was left at room temperature for 42 hours at pH 2.0 (H$_3$PO$_4$). Ethyl acetate was added, and the organic layer washed with water, dried and evaporated to give the title compound (0.05g), max (CHCl$_3$) 3360, 1790, 1750, 1700, 1530, 1500, 1355cm$^{-1}$. δ (CDCl$_3$) 1.23, 1.29 (6H,2s (CH$_3$)$_2$C), 3.31, 3.36 (3H,2s,CH$_3$O—), 4.29, 4.32 (1H,2s,C$_3$-proton), 7.0–7.8 (13H, complex, aryl and amide protons) 8.15 (2H, d,J. 8Hz, —CH—CNO$_2$—).

Method (ii)

The Ketenimine from Example 2 (0.05g) in aqueous acetone was stood at room temperature for 42 hours at pH 3.1 (p-toluenesulphonic acid added to give the required acidity). Ethyl acetate was added, and the organic layer washed with sodium bicarbonate solution and water. Drying and evaporation gave the title compound (0.05g).

EXAMPLE 4.

Preparation of p-nitrobenzyl-6β-(2'-phenyl-2'-phenoxycarbonyl)-Ketenimino-6α-methylthio penicillanate.

Method 1

The Ketenimine from Example 1 (0.15g., 0.28mmol) and methyl methanethiosulphonate (0.034ml, 0.29mmol) in dimethylformamide (1ml) were added to potassium carbonate (0.04g, 0.29mmol) at 0° C., and the mixture stirred for 45 minutes. Ether and ammonium chloride solution were added, and the organic layer was further washed with water dried (Na$_2$SO$_4$) and evaporated to give a residue which was chromatographed on silica (ethyl acetate/petrol). Collection of the mobile main component gave the title compound (0.05g, 31%), max(CHCl$_3$) 2010, 1785, 1730, 1525, 1350, 1190cm$^{-1}$. δ (CDCl$_3$) 1.34, 1.38 (6H, 2s, (CH$_3$)$_2$C), 2.39 (3H,s,CH$_3$S—), 4.43 (1H,s,C$_3$-proton), 5.35 (2H,s,—CH$_2$—), 5.53 (1H,s,C$_5$-proton), 7.2–7.8 (12H, complex, aryl protons), 8.27 (2H,d,J 8.5 Hz., —CH—NO$_2$).

Method 2

The Ketenimine from Example 1 (0.15g., 0.29mmol) in DMF (1ml) at −15° was added to sodium hydride (ca 55% mineral oil suspension 0.018g., ca. 0.37mmol) in DMF (3ml) at −20°. Methyl methanolsulphonate (0.034ml, 0.29ml) was added, and the mixture stirred at −10° for 70 minutes. Work up and chromatography as in Method 1 gave the title compound (0.04g., 29%).

Method 3

The Ketenimine from Example 1 (0.15g., 0.29mmol) in DMF (2ml) at −35° was added with stirring to potassium t-butoxide (31mg., 0.29mmol) in DMF (4ml) at −35°. Methyl methanolthiosulphonate (0.034ml, 0.29mmol) was immediately added, and the solution stirred for 1 hour at −35°. Work up and chromatography as in Method 1 gave the title compound (0.04g, 29%.

EXAMPLE 5

Preparation of 2'-epimers of p-nitrobenzyl 6β-(2'-phenyl-2'-phenoxycarbonyl)acetamido-6α-methylthio penicillanate.

The methylthio Ketenimine from Example 4 (0.07g) was dissolved in aqueous T.H.F. (5ml), the pH of which had been lowered to 1.0 by the addition of phosphoric acid. After 72 hours at room temperature, ethyl acetate was added, and the organic phase washed with water, dried (Na$_2$SO$_4$) and evaporated to give the title compound (0.06g). max(CHCl$_3$) 3300, 1780, 1745, 1685, 1525, 1350cm$^{-1}$. δ (CDCl$_3$) 1.26, 1.34, 1.41, (6H,3s,(CH$_3$)$_2$C), 2.19, 2.26 (3H,2s, CH$_3$s—), 4.36, 4.40 (1H,2s,C$_3$-proton), 4.92 (1H,s,—CH—CON), 5.36 (2H,s,—CH$_2$Ar), 5.61–5.64 (1H,2s,C$_5$-proton), 7.0—7.9 (13H, complex, aryl and amide protons), 8.30 (2H,d,J 8Hz, —CH—CNO$_2$—).

EXAMPLE 6

Preparation of p-nitrobenzyl 6β-(2'(3''-thienyl)-2'-p-methylphenoxycarbonyl)-Ketenimino penicillanate.

p-Nitrobenzyl 6β-(2'-(3''-thienyl)-2'-p-methylphenoxycarbonyl)acetamido penicillanate (3.57g, 5.86mmol) in benzene (18ml) was treated dropwise at 5° with pyridine (4.29ml) and subsequently with phosphorus pentachloride (3.72g) in benzene (75ml), at such a rate to keep the temperature at 5° C. After three hours stirring the solution was filtered, the solids washed with water and sodium bicarbonate solution. Drying and evaporation gave the title compound (3.35 g, 97%), max (CHCl$_3$) 2010, 1745, 1725, 1525, 1345cm$^{-1}$., δ (CDCl$_3$) 1.38, 1.49 (6H,2s,(CH$_3$)$_2$C), 2.26 (3H,s, CH$_3$Ar) 4.38 (1H,s, C$_3$-proton), 5.25 (2H,s,—OCH$_2$Ar), 5.52 (2H,s,C$_5$ and C$_6$ protons), 6.9–7.7 (9H,complex, aryl and thienyl protons), 8.15 (2H,d,J 8Hz, —CH—CNO$_2$—).

EXAMPLE 7

Preparation of p-nitrobenzyl 6α-methoxy-6β-(2'-(3''-thienyl)-2'-p-methylphenoxycarbonyl)Ketenimino penicillanate.

Method 1

The Kentenimine from Example 6 (2.50 g., 4.21mmol) in T.H.F. (30ml) at −70° was treated with chlorine (4,2mmol), and the solution stirred for 20 minutes. Lithium methoxide (0.44 g., 11.5 mmol) in methanol (12ml) was added at such a rate (5 minutes) that the temperature stayed below −67° C. After 10 minutes further, acetic acid (4ml) was added, and the solution was removed from the cooling bath. Ethyl acetate was added, and the organic layer washed with sodium bicarbonate and brine, dried and evaporated to give the crude title compound (2.42 g.). Purification is achieved by chromatography on silica (petrol/ethyl acetate), giving 40% yield overall. The title compound possesses max(CHCl$_3$) 2010, 1790, 1750, 1725, 1525, 1345cm$^{-1}$. δ (CDCl$_3$) 1.34 (6H,s,(CH$_3$)$_2$C), 2.23 (3H,s,CH$_3$Ar), 3.58 (3H,s,OCH$_3$), 4.36 (1H,s,C$_3$-proton), 5.23 (2H,s,—CH$_2$Ar) 5.53 (1H,s,C$_5$-proton), 6.8–7.7 (5H, complex, aryl and thienyl protons, 8.16 (2H,d,J 8Hz,—CH-13 CNO$_2$).

Method 2

Substitution of sodium bicarbonate for lithium methoxide (molar proportions as Method 1) as used in Method 1 gave the title compound in slightly lower yield than in Method 1.

Method 3

Substitution of bromine for chlorine (molar proportions as Method 1) as used in Method 1 gave the title compound in lower yield than in Method 1.

EXAMPLE 8

(a) Preparation of 2''-epimers of p-nitrobenzyl 6α-methoxy-6β-(2'-(3''-thienyl)-2'-p-methylphenoxycarbonyl)-acetamido penicillanate.

The Ketenimine from Example 7 (1.67 g., 2.69mmol) was dissolved in T.H.F. (30ml) containing water (1ml) and a few drops of H$_3$PO$_4$ to lower the pH to 2.6. After three days standing at room temperature, ethyl acetate was added, and washed with water. Drying and evaporation gave the title compound (1.51 g., 88%) max (CHCl$_3$) 3350, 1790, 1750, 1700, 1525, 1350cm$^{-1}$. δ (CDCl$_3$) 1.29, 1.33 (6H,2s,(CH$_3$)$_2$C), 2.27 (3H,s,CH$_3$Ar), 3.33, 3.38 (3H,2s,CH$_3$O—), 4.31, 4.33 (1H,2s, C$_3$-proton), 4.87 (1H,s,—CH—CON), 5.28 (2H,s,—OCH$_2$Ar), 5.57 (1H,s,C$_5$-proton), 6.8–7.6 (10H, complex, aryl, thienyl and amide protons), 8.17 (2H,d,J 8Hz, —CH—C-NO$_2$—).

(b) 2'-epimers of 6α-methoxy-6β-methoxy-6β-(2'(3''-thienyl)-2'-p-methylphenoxycarbonyl)acetamido penicillanic acid.

The p-nitrobenzyl ester from (a) above (1.0 g., 2.59mmol) in ethanol (15ml): T.J.F. (4ml): water (a few drops) was hydrogenated overPd/C (10%; 1g) for four hours. The solution was filtered the solids washed with acetone, and the combined solutions evaporated to give the title compound the hydrogenolysed p-toluidene (total weight, 0.89 g.). The latter material was removed by precipitation of the penicillin as the sodium salt from acetone; ether with sodium 2-ethyl hexanoate in methyl isobutyl ketone (2N., 0.73ml). (Overall yield from ester: 76%).

(c) 2'-epimers of 6α-methoxy-6β-(2'(3''-thienyl)-2'-carboxy acetamido penicillanic acid.

The monoester from (b) above (5.66 g., 10.5mmol) in water (20ml) was stirred for 2 hours with Na$_2$B$_4$O$_7$ decahydrate (8.2 g). The pH was adjusted to 4, and the solution washed with ethyl acetate.

The pH was then lowered to 2, and the solution extracted with ethyl acetate. Drying and evaporation gave the title compound (3.5 g.) which was precipitated as the di-sodium salt from acetone with sodium 2-ethyl hexanoate in methyl isobutyl ketone (2N, 9.0ml). (Overall yield from ester: 74%). The di-sodium salt possess max (nujol) 1760, 1670, 1600cm$^{-1}$, δ(D$_2$O) 1.44 (6H,s,(CH$_3$), 3.51, 3.60 (3H,2s,—OCH$_3$), 4.34 (1H,s,C$_3$-proton), 5.61 (1H,s,C$_5$-proton), 7.1–7.7 (3H, complex, thienyl protons).

EXAMPLE 9

Preparation of p-bromophenacyl 6β-(2'(3''-thienyl)-2'-p-methylphenoxycarbonyl)-Ketenimino penicillanate.

p-Bromophenacyl 6β-(2'-(3''-thienyl)-2'-p-methylphenoxycarbonyl) acetamido penicillanate (0.89 g, 1.33mmol) in benzene (5ml) was treated successively at 5° C. with pyridine (1.02ml) and phosphorus pentachloride (0.84 g) in benzene (20ml). After stirring for three hours, solids were filtered and washed with ethyl acetate, and the organic solution washed with water, sodium bicarbonate and brine. Drying and evaporation gave the title compound (0.87 g., 95%). max (CHCl$_3$) 2040, 1790, 1750, 1700cm$^{-1}$. δ (CDCl$_3$) 1.64, 1.67 (6H,2s,(CH$_3$)$_2$C), 2.33 (3H,s,CH$_3$Ar), 4.64 (1H,s,C$_3$-proton), 5.37 (2H,ABq,J 17Hz, —OCH$_2$COAr). 5.64 (2H,s,C$_6$-protons), 7.0–7.9 (11H, complex, thienyl and aryl protons).

EXAMPLE 10

Preparation of p-bromophenacyl 6α-methoxy-6β-(2'-(3''-thienyl)-2'-p-methylphenoxycarbonyl)Ketenimino penicillante.

Method 1

The Ketenimine from Example 9 (0.32g., 0.54mmol) in T.H.F. (10ml) at −70° C. was treated with chlorine (0.54mmol) and stirred for 10 minutes. Sodium methoxide in methanol (1M. solution, 1.5ml) was added, and the solution stirred for a further 10 minutes at −70°. Acetic acid (0.5ml) was added, followed by ethyl acetate, and the organic solution was washed with sodium bicarbonate solution and brine to give the crude title compound (0.32g). Purified material was obtained by chromatography on silica (petrol/ethyl acetate). The title compound possesses max (CHCl$_3$) 2040, 1790, 1750, 1700cm$^{-1}$. 8 (CDCl$_3$) 1.52, 1.66 (6H,s,(CH$_3$)$_2$C), 2.38 (3H,s,CH$_3$Ar, 3.78 (3H,s,—OCH$_3$), 4.68 (1H,s,C$_3$-proton), 5.48 (2H,s,—OCH$_2$COAr), 5.68 (1H,s,C$_5$-proton,), 7.1–8.0 (11H,complex, thienyl and aryl protons).

Method 2

Substitution of bromine for chlorine as used in Method 1 (molar proportions as in 1) gave a lower yield of title compound than Method 1.

Method 3

Substitution of lithium methoxide for sodium methoxide, and bromine for chlorine as used in Method 1 (molar proportions as in 1) gave a lower yield of title compound than Method 1.

Method 4

The Ketenimine from Example 9 (0.25g., 0.42mmol) in T.H.F. (2ml) at $-70°$ was treated with bromine (0.023ml., 0.42mmol). After 10 minutes the T.H.F. solution was mixed with thallium (I) methoxide (1.1mmol) suspension in methanol (1ml) pre-cooled to $-50°$ C., and the mixture vigorously stirred for 30 minutes at $-50°$. Acetic acid (0.5ml) was then added, the precipitate filtered and ethyl acetate added. Washing with sodium bicarbonate solution and water, drying and evaporation gave the crude title compound (0.22g) in slightly lower purity than in Method 1.

EXAMPLE 11

(a) Preparation of 2'-epimers of p-bromophenacyl 6α-methoxy-6β-(2'-(3''-thienyl)-2'-methylphenoxycarbonyl) acetamido penicillanate.

The purified Ketenimine from Example 10 (0.30g., 0.44mmol) was dissolved in T.H.F. (5ml) containing water (0.2ml) and phosphoric acid, sufficient to lower the pH to 2.6. After three days at room temperature, ethyl acetate was added, and washed with water. Drying and evaporation gave the title compound (0.26g., 84%). max (CHCl$_3$), 3350, 1780, 1760, 1750, 1690cm$^{-1}$. 8 (CHCl$_3$), 1.40, 1.60 (6H,2s,(CH$_3$), 2.34 (3H,s,CH$_3$Ar), 3.45, 3.49 (3H,2s,CH$_3$O—), 4.61 (1H,s,C$_3$-proton), 5.16 (1H,s,—CH—CON), 5.44 (2H,s,—OCH$_2$CO$_2$Ar), 5.71 (1H,s,C$_5$-proton), 6.9–8.1 (12H,complex, thienyl, aryl, and amide protons).

(b) Preparation of 2'-epimers of 6α-methoxy-6β-(2'-(3''-thienyl)-2'-p-methylphenoxycarbonyl)acetamido penicillanic acid.

Method 1

The p-bromophenacyl ester from (a) above (0.26g) in dimethylformamide (6ml): acetic acid (3ml) was stirred with zinc dust (0.7g) for 75 minutes at room temperature. The solution was filtered and solids washed with ethyl acetate. The organic layer was washed with water and extracted with sodium bicarbonate solution. The aqueous layer was acidified to pH 1.8 and extracted with ethyl acetate. Drying and evaporation gave the title compound (40mg). max (CHCl$_3$) 3400–2400 (br), 1775, 1740, 1695cm$^{-1}$. 8(CDCL$_3$) 1.39, 1.51 (6H,2s,(CH$_3$)$_2$C), 2.38 (3H,s,CH$_3$Ar), 3.50 (3H,s,—OCH$_3$), 4.47 (1H,s,C$_3$-proton), 5.10 (1H,s,—CH—CON), 5.67 (1H,s,C$_5$-proton), 7.0–8.2 (9H, complex, thienyl, aryl, acid and amide protons).

(c) The 2'-epimers of 6α-methoxy-6-β-(2'-(3''-thienyl)-2'-carboxy) acetamido penicillanic acid were prepared as described in Example 8(c).

EXAMPLE 12

Preparation of p-bromophenacyl 6β-(2'-benzyloxycarbonyl-2'-(3''-thienyl))ketenimino penicillanate.

p-Bromophenacyl 6β-(2'-benzyloxycarbonyl-2'-(3''-thienyl))-acetamido penicillanate (0.89g., 1.33mmol) in benzene (5ml) was treated dropwise at 5° with pyridine (1.02ml), and subsequently with phosphorus pentachloride (0.84g) in benzene (20ml), at such a rate to keep the temperature at 5° C. After three hours stirring, the solution was filtered the solids washed with ethyl acetate, and the organic solution washed with water and sodium bicarbonate solution. Treatment with charcoal, drying and evaporation gave the title compound (0.70g., 76%). max (CHCl$_3$) 2030, 1790, 1760, 1750cm$^{-1}$. 8 (CDCl$_3$) 1.59, 1.63, (6H,2s,(CH$_3$)$_2$C), 4.59 (1H,s,C$_3$-proton), 5.28 (2H,s,—CH$_2$Ph), 5.39 (2H,ABq, J 17Hz, —CH$_2$COAr), 5.55 (2H,ABq, J 4Hz, C$_5$ and C$_6$ protons), 6.9–7.7 (12H, complex, aryl and thienyl protons).

EXAMPLE 13

Preparation of p-bromophenacyl 6β-(2'-o-isopropylphenoxycarbonyl-2'-(3''-thienyl)-)Ketenimino penicillanate.

p-Bromophenacyl 6β-(2'-o-isopropylphenoxycarbonyl-2'-(3''-thienyl)) acetamido penicillanate (0.44g., 0.63mmol) in benzene (3ml) was treated with pyridine (0.48ml) and phosphorus pentachloride (0.40g) in benzene (10ml) under the same conditions as used in Example 12. Work up as in Example 12 gave title compound (0.35., 82%). max (CHCl$_3$) 2000, 1785, 1750, 1700cm$^{-1}$. 8(CDCl$_3$) 1.21 (6H, d,J 7Hz, (CH$_3$)$_2$CH), 1.65 (6H,s,(CH$_3$)$_2$C), 3.05, sept, J 7 Hz., —CHMe$_2$), 4.63 (1H,s,C$_3$-proton), 5.44 (2H,ABq,J 17Hz., —CH$_2$COAr), 5.65 (2H,s,C$_5$ and C$_6$-protons), 7.1–8.0 (11H, complex, thienyl and aryl protons).

EXAMPLE 14

Preparation of p-bromophenacyl 6β-(2'-methoxycarbonyl-2'-(3''-thienyl)Ketenimino penicillanate.

p-Bromophenacyl 6β-(2'-methoxycarbonyl-2'-(3''-thienyl))acetamido penicillanate (0.49g., 0.82mmol) in benzene (5ml) was treated with pyridine (0.63ml) and phosphorus pentachloride (0.52g) in benzene (15ml) under the same conditions as used in Example 12. Work up as in Example 12 gave the tltle compound (0.35g., 74%). max (CHCl$_3$) 2000, 1780, 1750, 1700cm$^{-1}$. 8 (CDCl$_3$) 1.67 (6H,s,(CH$_3$)$_2$C), 3.69 (3H,s,—OCH$_3$), 4.67 (1H,s,C$_3$-proton), 5.45 (2H,ABq, J 18Hz., —CH$_2$COAr), 5.66 (2H,ABq, superimposed as "t", "J" 5Hz., C$_5$ and C$_6$-protons), 7.0s–8.0 (7H, complex, thienyl and aryl protons).

What we claim is:

1. A ketenimine, having the formula (I):

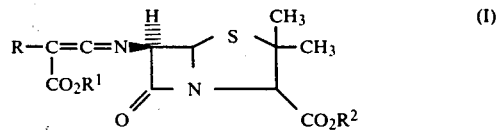

wherein R is 2-thienyl, 3-thienyl, phenyl or 4-hydroxyphenyl;

$CO_2R^1$ represents an esterified α-carboxy group; and
$CO_2R^2$ represents an in vivo hydrolysable esterified 3-carboxy group or a carboxylic acid salt, ester or anhydride.

2. A ketenimine as claimed in claim 1 wherein R is phenyl.

3. A ketenimine as claimed in claim 1 wherein R is 3-thienyl.

4. A ketenimine as claimed in claim 1 wherein $R^1$ is $C_{1-6}$ alkyl, benzyl, phthalidyl, indanyl, phenyl, mono-, di-, and tri-$(C_{1-6})$alkyl substituted phenyl.

5. A 6α-methoxy ketenimine of formula (V):

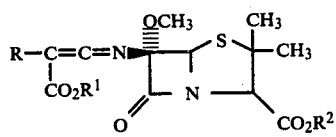
(V)

wherein R and $CO_2R^1$ are as defined in claim 1 except that $R^1$ is not an alkyl ester forming group and $CO_2R^2$ is an in vivo hydrolysable esterified 3-carboxy group.

6. A ketenimine as claimed in claim 5 wherein R is 2- or 3-thienyl, phenyl or 4-hydroxyphenyl.

7. A ketenimine as claimed in claim 6 wherein R is phenyl.

8. A ketenimine as claimed in claim 6 wherein R is 3-thienyl.

9. A ketenimine as claimed in claim 5 wherein $R^1$ is benzyl, phthalidyl, indanyl, phenyl, mono-, di-, and tri-$(C_{1-6})$alkyl substituted phenyl.

10. p-nitrobenzyl 6β-(2'-phenoxycarbamyl ketenimino penicillanate.

11. p-Nitrobenzyl 6β-(2'-(3''-thienyl)-2'-methylphenoxycarbonyl) ketenimino penicillanate.

12. p-Bromophenacyl 6β-(2'-(3''-thienyl)-2'-p-methylphenoxycarbonyl) ketenimino penicillanate.

13. p-Bromophenacyl 6β-(2'-benzyloxycarbonyl-2'-(3''-thienyl))ketenimino penicillanate.

14. p-Bromophenacyl 6β-(2'-o-isopropylphenoxycarbonyl-2'-(3''-thienyl))ketenimino penicillanate.

15. p-Bromophenacyl 6β-(2'-methoxycarbonyl-2'-(3''-thienyl))ketenimino penicillanate.

* * * * *